(12) United States Patent
Krill et al.

(10) Patent No.: US 6,482,964 B1
(45) Date of Patent: Nov. 19, 2002

(54) PROCESS FOR THE PREPARATION OF β-ISOPHORONE EPOXIDE

(75) Inventors: Steffen Krill, Hanau (DE); Klaus Huthmacher, Gelnhausen (DE); Alexander Möller, Gelnhausen (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/855,837

(22) Filed: May 16, 2001

(30) Foreign Application Priority Data

May 17, 2000 (DE) .......................................... 100 24 265

(51) Int. Cl.$^7$ ............................................ C07D 301/14
(52) U.S. Cl. ........................................ 549/525; 549/546
(58) Field of Search .................................. 549/525, 546

(56) References Cited

U.S. PATENT DOCUMENTS 4,168,274 A    9/1979  Hildon et al. .......... 260/348.25

FOREIGN PATENT DOCUMENTS

GB    1 188 791    4/1970

OTHER PUBLICATIONS

M. Constantino et al. "Uma Sintese Formal De Capsorubina" *Quimica Nova*, vol. 14, No. 1, 1991, pp. 22–25.

*Primary Examiner*—Ba K. Trinh
(74) *Attorney, Agent, or Firm*—Smith, Gambrell & Russell, LLP

(57) ABSTRACT

Process for the selective preparation of β-isophorone epoxide by epoxidation of β-isophorone with organic percarboxylic acids at a water content of less than 5 wt. %.

8 Claims, No Drawings

PROCESS FOR THE PREPARATION OF β-ISOPHORONE EPOXIDE

INTRODUCTION AND BACKGROUND

The present invention relates to a process for the preparation of β-isophorone epoxide (β-IPO, 1,5,5-trimethyl-7-oxa-bicyclo-[4,1,0]-heptan-3-one) by epoxidation of β-isophorone (β-IP, 3,5,5-trimethylcyclohex-3-en-1-one), wherein there is used as the oxidizing agent an organic per-acid in the form of its solution in an inert organic solvent.

The β-isophorone epoxide obtained in that process can be converted directly to hydroxyisophorone (HIP) by isomerization in the presence of suitable catalysts. 3,5,5-Trimethyl-4-hydroxy-cyclohex-2-en-1-one (HIP) is described in the literature as an aromatic substance and a fragrance (JP-OS 81 35 990; CH-PS 549 961; DE-OS 22 02 066). Its use as a flavouring auxiliary for foodstuffs is also known (CH-PS 549 956; M. Ishikara et al., J. Org. Chem. 1986, 51, 491 ff). Hydroxyisophorone is also a widely usable synthesis component for natural substances and pharmaceuticals (N.S. Zarghami et al., Phytochemistry 1971, 10, 2755 ff; J.N. Marx and F. Sondheimer, Tetrahedron Lett., Suppl. No. 8, Pt 1, 1–7, 1966).

In particular, β-IPO is an important intermediate for the synthesis of 2,6,6-trimethylcyclohexane-1,4-dione and hence for vitamin E. The synthesis sequence that is conventionally followed proceeds according to the following scheme:

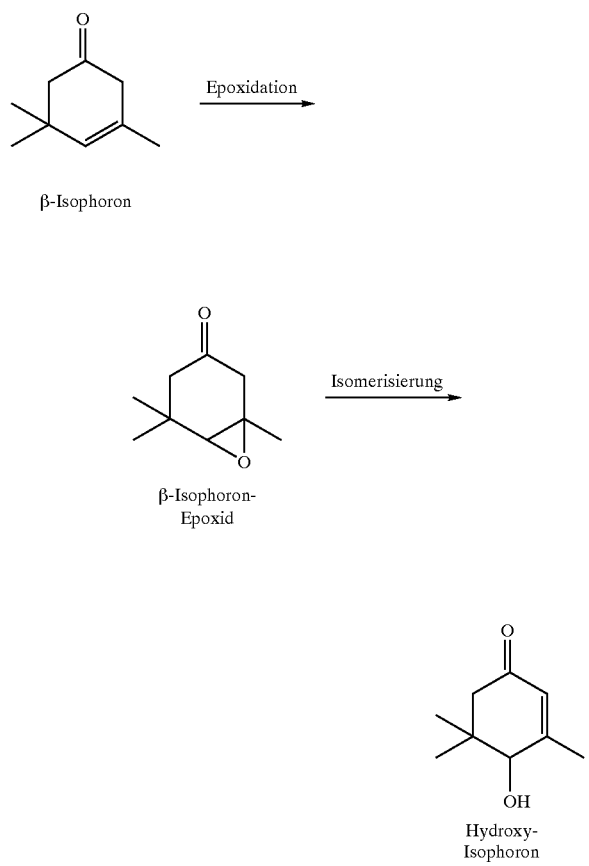

β-Isophoron

β-Isophoron-Epoxid

Hydroxy-Isophoron

The known processes for the preparation of β-IPO produce only unsatisfactory yields. It has been found that the oxidation of β-isophorone usually proceeds to 4-oxo-isophorone, hydroxyisophorone being formed in concentrations of from 1 to 50% depending on the oxidizing agent used. According to the described processes, the formation of hydroxyisophorone appears to be a secondary reaction. When the progress of the reaction is monitored, it is found that hydroxyisophorone is not the intermediate of 4-oxo-isophorone, since hydroxyisophorone is virtually inert under the oxidizing conditions.

The epoxidation of β-isophorone goes back to Isler et al. (Helv. Chim. Acta 39, 1956, 2041 ff), who carries out the epoxidation with peracetic acid as the oxidizing agent in acetic acid as the solvent and, after adjusting the pH value to from 8 to 9 using aqueous sodium hydroxide solution, isolates only HIP in unsatisfactory yields. Nor do Zarghami et al. (Phytochemistry 10, 1971, 2755 ff) disclose any yields of β-IP epoxide in their reaction with peracetic acid. A further description of the epoxidation of β-isophorone is to be found in Tetrahedron Lett. Suppl. No. 8, Pt. 1, 1966, 1–7. There are described organic solvents such as chloroform with the use of meta-chlorobenzoic acid as the oxidizing agent, m-chlorobenzoic acid precipitating from the solution after completion of the redox reaction and a product pattern being obtained that is composed of β-IP epoxide and HIP in a ratio of 1:1, and alpha-isophorone. It is evident that, according to that process, neither the undesired back-isomerization to alpha-IP nor the consecutive reaction to HIP can be suppressed. After hydrolysis at basic pH, 87% HIP are isolated.

A common feature of all those processes is that β-isophorone epoxide is obtained in unsatisfactory yields, which can be attributed to the fact that the reaction is carried out non-selectively, or to unsuitable oxidizing agents, or to the presence of water in the reaction medium, which both catalyses the back reaction of β-isophorone and destabilises the epoxide. From the β-IP epoxide, the diol that forms can also be demonstrated by addition of water.

A further reaction that is observed when there is inadequate monitoring of the reaction is the epoxidation of alpha-IP (which is formed in situ from β-IP by isomerization) to alpha-IP epoxide, and the consecutive reaction thereof, with isomerization, to 2-hydroxy-isophorone. Those basic secondary reactions are also observed in the case of epoxidation with other substrates, wherein diols and hydroxy esters in particular are obtained (see W. M. Weigert, Wasserstoffperoxid und seine Derivate, Hythig Verlag Heidelberg 1978, page 79 ff).

The possible secondary and consecutive reactions in the case of β-IP epoxidation are shown diagrammatically in the following scheme:

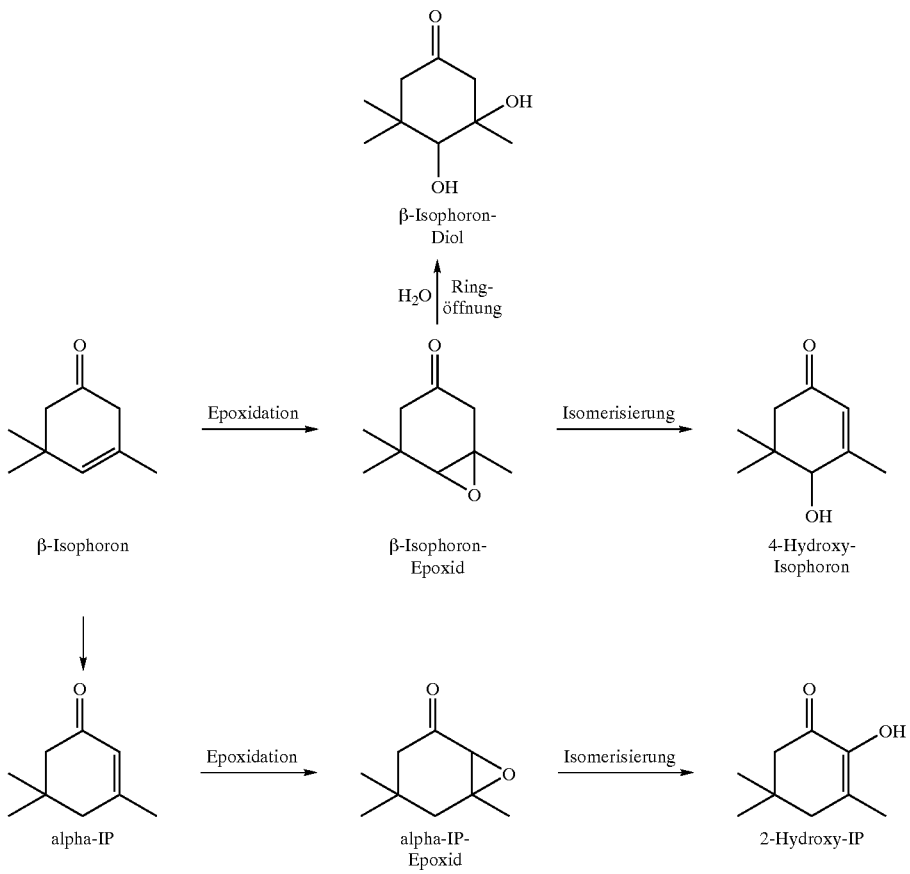

The epoxidation of β-isophorone is also described in the presence of anhydrous peroxidation reagents such as alkyl hydroperoxides (Hutter, Baiker et al., Journal Mol. Cat. 172, 427–435, 1997). A heterogeneous $SiO_2$—$TiO_2$ mixed oxide contact mass activates the peroxide, wherein, in order to achieve high selectivities, inter alia in order to suppress the formation of HIP, expensive pretreatment of the catalyst is necessary or, alternatively, additional auxiliary substances such as bases must be added. Although the best epoxide selectivities hitherto have been achieved by that process, the use of alkyl hydroperoxides, which are consumed stoichiometrically, for carrying out an industrial process is disadvantageous. Furthermore, it is not desirable to use a heterogeneous contact mass which must be prepared in an expensive manner.

DP 38 06 835 describes the oxidation of β-IP by reaction with aqueous hydrogen peroxide in the presence of formic acid to form HIP. β-IP epoxide is obtained as an intermediate in that process, but a rate of back-isomerization of the order of from 20 to 35% makes the process less attractive from an industrial point of view.

No process has hitherto been known that permits the preparation of β-IP epoxide using inexpensive oxidizing agents that are obtainable efficiently industrially, and with a high product selectivity. The objects to be achieved by the invention are derived therefrom.

An object of the present invention is to prepare β-isophorone with high selectivity and in a high yield starting from β-isophorone, wherein, especially, the back-isomerization of the starting material to alpha-isophorone is to be suppressed, in order to prevent alpha-IP having to be separated from the product solution in an expensive manner, the consecutive reaction to the diol in the presence of water is to be suppressed, and industrially inexpensive oxidizing agents, especially hydrogen peroxide or a per-acid, are to be used as the epoxidizing agent.

A further object of the invention is to find a process for the conversion of β-isophorone, wherein the per-acid is prepared in a preliminary step by the reaction between the corresponding organic carboxylic acid, water-containing hydrogen peroxide and sulfuric acid, and, by means of suitable process-related measures, in preparing the resulting per-acid solution so that it is suitable for the selective epoxidation of β-isophorone.

SUMMARY OF THE INVENTION

The above and other objects of the invention can be achieved by bringing β-isophorone into contact, at moderate temperatures, with an anhydrous organic per-acid dissolved in an organic solvent, the organic solvent at the same time also being the extracting agent for the extraction of the organic per-acid during its preparation. According to the understanding of the person skilled in the art, the percarboxylic acid designated anhydrous may generally still contain up to 5 wt. %, especially from 0.01 to 5 wt. %, water.

According to the process it is possible to work with inexpensive raw materials such as aqueous hydrogen peroxide on the one hand and organic carboxylic acid and a solvent on the other hand, only the starting material substrate β-isophorone and hydrogen peroxide being consumed in the epoxidation process and it being possible to recirculate most of the other raw materials.

A further aspect of the process according to the invention relates to the safe handling of the substances used or the peroxide mixtures formed in situ, especially the per-acid dissolved in the solvent together with hydrogen peroxide. According to the prior art (DP 38 06 835), high temperatures of about 60° C. must be ensured for the reaction in order to achieve at least adequate reaction velocities, which is harmful in terms of safety when working with performic acid. Furthermore, in that process hydrogen peroxide is used in excess relative to the formic acid that is employed, which means a considerable specific consumption and also poses problems in terms of safety.

The invention relates to a novel process for the preparation of β-isophorone epoxide by oxidation of β-isophorone (β-IP) by reaction with an anhydrous per-acid in the form of its solution in a suitable solvent that is stable under reaction conditions, in the liquid phase, a two-phase mixture, which occurs in the case of a relatively high water concentration in the reaction mixture, essentially being avoided. In the simplest case of the process according to the invention, the solvent used for the oxidation is also the extracting agent for the corresponding per-acid in the preparation thereof from an aqueous hydrogen peroxide solution, the carboxylic acid and sulfuric acid.

DETAILED DESCRIPTION OF INVENTION

The reaction takes place at temperatures of from -50°C. to 100° C., the operation being carried out in a preferred embodiment at from 0° C. to 60° C. In that temperature range for implementation as an industrial process, the reaction times are sufficiently quick to achieve complete conversion of β-isophorone. Although higher temperatures are also suitable for carrying out the reaction, the proportion of hydroxyisophorone is increased by that measure. At lower temperatures, high product selectivities can be achieved, but the reaction velocity falls and it is necessary to work with cooling brine.

The ratio between β-isophorone and the per-acid used as oxidizing agent is not critical for the product selectivity and may be chosen, depending on the procedure, in a molar ratio of β-IP:percarboxylic acid=from 10:1 to 1:10. A preferred molar ratio of the components is the range from 2:1 to 1:2. In view of the potential risks involved when working with per-acids, it is expedient to use the epoxidizing agent in a slightly deficient amount as compared with β-isophorone so that, when the reaction is complete, the peracid has been converted with formation of the corresponding carboxylic acid and only a small concentration of excess β-isophorone is present. During working up, the unconverted β-isophorone may either be recycled as such or alternatively, after isomerization to alpha-IP, it may be fed back to the β-IP preparation process again.

The concentration of per-acid in the extracting agent or in the solvent used in the oxidation may be from 1 wt. % to 50 wt. %, the operation being carried out, in view of safety-related criteria, in a preferred range of from 5 wt. % to 30 wt. %. The maximum concentration range to be chosen of the per-acid in the organic solvent must be made dependent especially on the choice of per-acid used, of solvent and of oxidation temperature.

A large number of conventional organic solvents may be used as the solvent for the oxidation or as the extracting agent for the per-acid.

The β-isophorone epoxide obtained at the end of the reaction may be reacted further directly under suitable conditions after isolation. It is expedient especially to react β-IPO, after isolation, to hydroxyisophorone or to 2,2,6-trimethyl-cyclohexane-1,4-dione (DH-KIP=dihydro-ketoisophorone) according to known processes.

The organic carboxylic acid used in the present process is preferably an aliphatic, alicyclic, aromatic carboxylic acid having from 1 to 20 carbon atoms, it being possible for the hydrocarbon radical to carry one or more functional groups. Especially preferred carboxylic acids that form percarboxylic acids are formic acid, acetic acid, propionic acid, butyric acid, valeric acid and higher homologues. There may be mentioned as examples of branched derivatives that may be used isobutyric acid, pivalic acid and neopentylcarboxylic acid. There may be mentioned as examples of aromatic, substituted and unsubstituted carboxylic acids that form percarboxylic acids benzoic acid, m-chloro- and p-nitro-benzoic acid, or also monoterephthalic acid. Halogenated derivatives, such as, for example, trihalogenated acetic acid (trichloric, trifluoric acid), are also suitable.

The preparation of the per-acid from the corresponding carboxylic acid is known per se. The preparation is to be explained in an embodiment using the formation of peracetic acid as an example. Acetic acid is usually allowed to react with aqueous hydrogen peroxide in the presence of an acid catalyst (in the case of carboxylic acids activated by corresponding substituents and having sufficient acidity, no additional catalytic acid must be added. Formic acid in the presence of hydrogen peroxide also forms performic acid in situ without its being necessary additionally to add a mostly mineral catalytic acid).

Sulfuric acid is conventionally employed as the catalytic acid. Mixing carboxylic acid/aqueous hydrogen peroxide/sulfuric acid yields more or less pure, aqueous solutions of peracetic acid and, after equilibrium has been attained, a so-called equilibrium peracetic acid having the following composition (Ullmanns Enzyklopädie der technischen Chemie, 3rd edition, Vol. 13, p. 254):

| peracetic acid: | approx. from 40–42% |
|---|---|
| acetic acid: | approx. from 37–40% |
| water: | approx. from 10–14% |
| $H_2O_2$: | approx. from 4–6% |
| sulfuric acid: | approx. from 0.5–1%. |

Very clean aqueous solutions are obtained if, in addition to the catalytic acid and water, a molar quotient $H_2O_2$:per-acid of >1 is adjusted and, when attainment of equilibrium is complete, the per-acid is removed as an azeotropic mixture with water at reduced pressure at the head of a distillation column. According to DE-PS 11 65 576, anhydrous solutions of the per-acid in an organic medium can be prepared from those solutions. The anhydrous or low-water solution of the per-acid in an organic medium may also be prepared by azeotropic distillation of the water with a suitable solvent from the reaction mixture $H_2O_2$ —catalytic acid—carboxylic acid (see Ullmanns Enzyklopädie der technischen Chemie, Suppl. Volume, 3rd edition, p. 181). A further method, which in view of the safety risks involved in dealing with such solutions can be categorized as comparatively safe, is extraction of the per-acid using a suitable extracting agent directly from the aqueous solution containing the percarboxylic acid.

Suitable extracting agents within the scope of the invention are described in DE-OS 21 45 603, there being suitable inter alia aliphatic, cycloaliphatic, aromatic solvents, but also halogenated derivatives of compounds from those classes of substances, especially chlorinated hydrocarbons such as methylene chloride and chloroform. The hydrogen peroxide solutions used may have an $H_2O_2$ content of from 10 to 90 wt. %, there being used especially commercially available aqueous peroxide solutions having a content of from 30 to 85 wt. %, preferably a solution having a content of from 45 to 70 wt. %.

A solution that is likewise suitable for the epoxidation of β-isophorone can be prepared from mature solutions of percarboxylic acids by extraction using phosphoric acid esters, especially trialkyl phosphates according to U.S. Pat. No. 3,829,216. In that case, absorption with the mentioned phosphoric acid esters is first carried out, and then the 10 to 80 wt. % per-acid solutions are desorbed with an alkyl ester so that solutions of the per-acid in an alkyl ester are ultimately formed.

In a preferred embodiment of the process according to the invention, the low-water solution of the organic percarboxylic acid is prepared according to U.S. Pat. No. 4,904,821. That document describes the preparation of a percarboxylic acid solution in alkyl phosphates, by placing $H_2O_2$ (from 30 to 35 wt. % aqueous solution) and acetic acid in a molar ratio of from 1 to 2:1 in the base of a distillation column, adjusting the amount of sulfuric acid to from 20 to 30 wt. %, based on the mass of the total solution, and removing a mixture of acetic acid, peracetic acid and water via the head at temperatures of from 55 to 70° C. at reduced pressure. The vapours are absorbed in a suitable phosphoric acid trialkyl ester, while water that has not been absorbed can be removed via the head of that absorption column.

For the purposes of epoxidation, the solutions of the percarboxylic acid, together with the corresponding carboxylic acid, in the phosphoric acid ester are then used directly, or alternatively the solutions are transferred to another conventional solvent by desorption.

The contents of the percarboxylic acid solutions in the solvent or in the extracting agent are usually from 1 to 50 wt. %, with a dilution <30 wt. % preferably being aimed for in order to ensure safe handling.

The process according to the invention may be carried out, as described, in the presence of organic solvents that are inert under the reaction conditions. The concentration of the reactants in the solvent has only a negligible effect on the product pattern of the conversion and is dependent essentially on safety aspects. A solvent-free procedure may also be carried out, in which case β-isophorone is brought directly into contact with the per-acid-containing solution, if it is ensured that the water concentration of the per-acid-containing solution is sufficiently low that both back-isomerization to alpha-IP and consecutive reaction of the epoxide to HIP can largely be suppressed. The hydrogen concentration of the organic solution of the percarboxylic acid that is used is usually to be less than 5 wt. %, and the water content is preferably from 0.01 to 2 wt. %.

The solvents used must usually be stable in the presence of per-acids. A further selection criterion is that they must be readily separable by distillation from the carboxylic acid that is used and from the product.

If the epoxidation takes place in the presence of organic solvents, there are advantageously used aliphatic and cyclic esters, for example methyl acetate, ethyl acetate, propyl acetate, butyl acetate, isobutyl acetate, gamma-butyrolactone, ethylene carbonate, derivatives and homologues thereof, aliphatic, alicyclic and aromatic hydrocarbons, for example pentane, hexane, heptane, octane and further homologues, benzene, toluene, and xylene.

Ketones, such as, for example, acetone, methyl ethyl ketone, diethyl ketone and isophorone, are also suitable as solvents within the scope of the invention. Aliphatic, aromatic or mixed ethers, such as diethyl ether, methyl tert-butyl ether, may also be used, even though their usability is limited for safety reasons. Suitable organic phosphoric acid esters are those whose substituents contain from 3 to 30 hydrocarbons, for example phosphoric acid triesters whose substituents may be of aliphatic, alicyclic or aromatic nature. Mention may be made at this point of tricyclohexyl phosphate, triphenyl phosphate, tricresyl phosphate, diphenylcresyl phosphate, triethyl phosphate, tributyl phosphate, trioctyl phosphate and other derivatives and homologues.

Further suitable classes of solvents are halogenated hydrocarbons. Mixtures of the mentioned solvents may also be employed.

In an embodiment of the process according to the invention, the resulting β-isophorone epoxide is isolated directly after destruction of excess peroxide and per-acid. On a laboratory scale, it is also possible to extract by shaking with a small amount of aqueous sodium bisulfite solution until the peroxide test is negative. When working with excess β-IP, it is ensured, when the reaction is complete, that no excess per-acid is present in the product mixture. When the reaction is complete and interfering peroxides have been destroyed, a product mixture consisting essentially of carboxylic acid, β-IPO, hydroxyisophorone and the solvent is present. The carboxylic acid can be separated off and fed back by fractional distillation. A further possible method of separating off the organic carboxylic acid is extraction using a polar extracting agent that is immiscible with the organic phase and is inert towards the product. In the simplest case, the resulting carboxylic acid can be extracted using a small amount of water. Isolation of β-IPO is carried out by distillation, the solvent generally being the low-boiling component in respect of β-IPO. Where high-boiling absorbents, extracting agents or solvents are used, such as the mentioned phosphoric acid triesters, β-IPO may also be the readily volatile component. The reaction medium that remains may be fed back to the reaction again once the product has been separated off.

The purity of the β-isophorone epoxide so isolated corresponds to a product quality such as is required for use as a starting material for the synthesis of 4-hydroxyisophorone (HIP) and trimethylcyclohexane-1,4-dione (DH-KIP), the intermediates for various natural substances and vitamin E acetate.

The present invention will be further understood with reference to the following examples.

EXAMPLE 1

Conversion of β-isophorone Using Perpropionic Acid in Toluene

Under nitrogen, 37 g of propionic acid (0.5 mol) are placed at room temperature in a 250 ml three-necked flask. 34 g of a 50 wt. % hydrogen peroxide solution (i.e. 0.51 mol $H_2O_2$ and 0.94 mol water) and 15 g of concentrated sulfuric acid (0.15 mol) are simultaneously added to the solution, in the course of 5 minutes, with external cooling. The cooling and the corresponding rate of addition ensure that the temperature does not exceed 25° C. The molar quotient of $H_2O_2$: propionic acid:$H_2SO_4$ in the case of such stoichiometry is 1.5:1.5:0.45. When the resulting solution has been stirred at room temperature for 15 minutes, the solution is extracted using 2×100 ml of toluene, yielding 230 g of perpropionic acid in toluene which contains, in addition to per-acid and toluene, also unconverted propionic acid and $H_2O_2$. The solution of perpropionic acid in toluene, which still contains residues of $H_2O_2$ and unconverted propionic acid, is transferred to a 500 ml three-necked flask equipped with an internal thermometer, a dropping funnel and a gas bubble counter. Under nitrogen, 46 g of β-IP (GC content: 99.5%; 0.33 mol) are added dropwise in the course of 20 minutes while maintaining the solution at an internal temperature of 10° C. The mixture is allowed to react for one hour at 10° C. and for a further hour at room temperature. The resulting product solution in toluene is examined against an added internal standard (dodecane), the following results being obtained

| | |
|---|---|
| β-IP conversion: | 21.51 g (47.2%) |
| β-IPO yield: | 21.28 g (41.8% of theory) |
| β-IPO selectivity: | 88.6% of theory |
| alpha-IP selectivity: | 0.11 g (0.52%) |
| HIP selectivity: | 0.91 g (3.8%) |

The Example shows that, when propionic acid in toluene is used, it is possible to obtain good β-IPO selectivities while largely suppressing back-isomerization to alpha-IP and consecutive reaction to HIP.

EXAMPLE 2

Conversion of β-isophorone Using Perpropionic Acid in Benzene Under nitrogen, 37 g of propionic acid (0.5 mol) are placed at room temperature in a 250 ml three-necked flask. First 15 g of concentrated sulfuric acid (0.15 mol) and then 34 g of a 50 wt. % hydrogen peroxide solution (0.51 mol $H_2O_2$ and 0.94 mol water) are added to the solution in the course of 5 minutes, with external cooling. The molar quotient of $H_2O_2$:propionic acid:$H_2SO_4$ of the starting solution in the case of that stoichiometry is 3:3:0.9 (the values are based on the molar amount of β-IP to be oxidized).

By means of external cooling with an ice-bath it is ensured that the reaction temperature does not exceed 20° C., and stirring is carried out for a further 30 minutes. The solution so obtained is extracted using 3 ×60 ml of benzene. The extracted benzene phase is dried with $MgSO_4$, there being obtained after filtration a clear benzene phase containing perpropionic acid, propionic acid and hydrogen peroxide. A total of 38 g of the starting solution has been converted to the organic phase by extraction using benzene.

The solution of perpropionic acid in benzene is transferred to a 500 ml three-necked flask equipped with an internal thermometer, a dropping funnel and a gas bubble counter. Under nitrogen, 23 g of β-IP (GC content: 99.5%; 0.166 mol) are added dropwise in the course of 10 minutes while maintaining the solution at an internal temperature of 20° C. Stirring is continued for a further 90 minutes, and the progress of the reaction is monitored by means of GC.

After 95 minutes, the reaction is terminated, the mixture is cooled to room temperature, and the product solution in benzene is washed with a small amount of 10 wt. % aqueous $NaHSO_3$ solution. The results of the GC quantification of the product solution are as follows:

| | |
|---|---|
| β-IP conversion: | 22.25 g (97%) |
| β-IPO yield: | 23.8 g (93% of theory) |
| β-IPO selectivity: | 95.9% of theory |
| alpha-IP selectivity: | 0.03 g (0.14%) |
| HIP selectivity: | 0.32 g (1.3%) |

The Example shows that, when propionic acid in benzene is used, it is possible to obtain very good β-IPO selectivities while largely suppressing back-isomerisation to alpha-IP and consecutive reaction to HIP.

Comparison Example 1

Conversion of β-Isophorone Using 15 wt. % Aqueous Peracetic Acid 6.9 g of β-isophorone (50 mmol) are placed in a three-necked flask with magnetic stirring, and 50 g of a 15 wt. % peracetic acid (approx. 100 mmol) are slowly added dropwise over a period of 20 minutes in such a manner that the internal temperature of the solution did not exceed 25° C. The solution is initially two-phase, but becomes homogeneously single-phase in the course of the reaction. After 3 hours, the reaction is terminated and the results are quantified by means of GC:

| | |
|---|---|
| β-IP conversion: | 6.83 g (99%) |
| β-IPO selectivity: | 0.23 g (3.0% of theory) |
| alpha-IP selectivity: | 0.35 g (4.6 |
| HIP selectivity: | 3.08 g (40.4%) |

The corresponding β-IP diol is also detected with a selectivity of 8%, as well as further uncharacterised products. In total, the reaction is non-selective and unsuitable for the preparation of β-IP epoxide.

Further variations and modifications of the foregoing will be apparent to those skilled in the art and are intended to be encompassed by the claims appended hereto.

German priority document 100 24 265.0 is relied on and incorporated herein by reference.

We claim:

1. Process for the selective preparation of β-isophorone epoxide (1,5,5-trimethyl-7-oxa-bicyclo-[4,1,0]-heptan-3-one) in an epoxidation reaction:

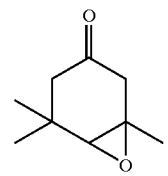

comprising epoxidizing β-isophorone (3,5,5-trimethylcyclohex-3-en-1-one)

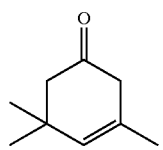

with an organic percarboxylic acids at temperatures of from −50° C. to 100° C., in a non-aqueous solution, the percarbonxylic acid is formed in a preceding equilibrium and is absorbed or extracted with the solvent of the oxidation.

2. Process according to claim 1, wherein the epoxidation is carried out with an organic per-acid in the form of its solutions in an organic solvent at temperatures of from 0 to 60° C.

3. Process according to claim 1, wherein the oxidizing agent is a member selected from the group consisting of performic acid, peracetic acid, perpropionic acid and homologous compounds or mixtures thereof.

4. Process according to claim 1, wherein the water content of the percarboxylic acid used is from 0.01 to 5 wt. %.

5. Process according to claim 1, wherein the organic per-acid is used in the form of its solution in an aromatic, aliphatic, or alicyclic hydrocarbon, the corresponding chlorinated derivative, or organic phosphoric acid triester or ester as solvent.

6. Process according to claim 1, wherein perpropionic acid or peracetic acid in benzene or toluene is used, or the solution of the corresponding per-acid, together with the non-oxidized carboxylic acid in phosphoric acid triesters is used as solvent.

7. Process according to claim 1, wherein the content of the per-acid in the solution in the organic solvent is from 0.1 to 60 wt. %.

8. Process according to claim 7, wherein the epoxidation is carried out in a molar ratio of percarboxylic acid:β-isophorone of from 10:1 to 1:10.

* * * * *